United States Patent [19]
Vanlerberghe et al.

[11] Patent Number: 5,985,255
[45] Date of Patent: Nov. 16, 1999

[54] FLUID COMPOSITION CONTAINING A WAX MICRODISPERSION AND A CATIONIC SURFACTANT, A METHOD FOR ITS PREPARATION AND USES THEREOF

[75] Inventors: Guy Vanlerberghe, Montjay La Tour; Luc Nicolas-Morgantini, Rully; Alain Lety, Lagny S/Marne, all of France

[73] Assignee: L'Oreal, Paris, France

[21] Appl. No.: 08/758,667

[22] Filed: Dec. 2, 1996

Related U.S. Application Data

[63] Continuation of application No. 07/658,644, Feb. 22, 1991, abandoned.

[30] Foreign Application Priority Data

Feb. 23, 1990 [FR] France ................................ 98 02295

[51] Int. Cl.⁶ .................................................... A61K 7/075
[52] U.S. Cl. ..................... 424/70.28; 424/70.1; 514/937; 514/938
[58] Field of Search .................................. 514/937, 938; 424/70.1, 70.28

[56] References Cited

FOREIGN PATENT DOCUMENTS 1269340  5/1978  France .
1312654  4/1973  United Kingdom .

OTHER PUBLICATIONS

Patent Abstract of Japan, vol. 13, No. 313 (C–618) [3661], Jul. 1989 & JP–A–1 096247.

French Search Report of 90 02295.

*Primary Examiner*—Thurman K. Page
*Assistant Examiner*—T. Ware
*Attorney, Agent, or Firm*—Nixon & Vanderhye, P.C.

[57] ABSTRACT

A fluid composition is provided in the form of a wax dispersion in a liquid vehicle which is comprised of a single phase. The dispersed phase is a stable microdispersion comprised of particles having a size lower than 0.5 μm. The particles are constituted essentially of a mixture of at least one wax, at least one emulsifying agent and optionally at least one oil and/or at least one liposoluble active ingredient. This mixture has a end melting point greater than 50° C. and lower than 100° C. The composition contains, by weight, from 0.1 to 40% of wax and from 0.01 to 25% of emulsifying agent. The emulsifying agent is a cationic emulsifier. The concentration of oil, when it is present, is less than or equal to 30 weight percent relative to the weight of the wax or mixture of waxes.

11 Claims, No Drawings

FLUID COMPOSITION CONTAINING A WAX MICRODISPERSION AND A CATIONIC SURFACTANT, A METHOD FOR ITS PREPARATION AND USES THEREOF

This is a Continuation of National application Ser. No. 07/658,644 filed Feb. 22, 1991, abandoned.

The present invention relates to a composition containing a wax microdispersion, as well as to a process for preparing said composition, and to their use.

French patent application No. 77.32762 (Publication No. 2.369.340) describes solid, liquid or pasty perfumed compositions, which contain fine particles having an average diameter between 0.1 and 200 µm, including up to 95% of a wax having a melting point ranging from 38 to 150° C. These particles serve as vehicles for a perfume, the perfume representing between 1 and 75% of the weight of the particles. The size of the particles preferably ranges from 1 to 100 µm, and more preferably, from 5 to 50 µm. These particles are incorporated into a support or a composition which contains a cationic surfactant. The solid particle constituents are mechanically fragmented and then ground, optionally in the presence of the other constituents when the composition being prepared is a liquid composition. The ground product can also be incorporated, by mixing, with a solid or liquid support. The resulting compositions, which are provided in the form of pastes, creams or liquid composition, are useful for conditioning textiles, as well as for conditioning of the hair.

It is also known that it is possible to obtain microemulsions with specific oils and microdispersions with certain waxes, which are stable and, for the latter, dilutable indefinitely in water, without aggregation or sedimentation of suspended particles. The wax microdispersions are obtained by melting the wax in the presence of an anionic or non-ionic surfactant, and optionally with some water, then with gradual addition of hot water with stirring. The intermediate formation of a water-in-oil type emulsion is observed, followed by a phase inversion with the final attainment of an oil-in-water type emulsion. On cooling a stable microdispersion of solid colloidal wax particles is obtained; see for instance "Microemulsions Theory and Practice", L. M. Prince, Ed., Academic Press (1977) pages 21–32. These wax microdispersions are used especially to brighten leather items as well as plastic ground coatings or coverings.

The waxes are natural substances (animal or vegetable) or synthetic. They are solid at ambient temperature (21° C.), and generally have certain a degree of plasticity. They are insoluble in water, soluble in oils, and can form waterproof films. These waxes are defined in, for instance, P. D. Dorgan, Drug and Cosmetic Industry, December 1983, pages 30–33, and Handbook of Cosmetic Science, H. W. Hibbot, ed., Pergamon Press, Oxford (1963) p. 60.

In the present invention a "microdispersion" is a dispersion that is obtained by the process described below, or by an analogous process.

It has now been discovered that such wax microdispersions can be obtained in the process that has been described above, by replacing the anionic or non-ionic surface active agent with a cationic surface active agent. The new resulting compositions exhibit interesting properties. They can be used, for instance, as maintenance agents (self-luster products) for leather items, ground coverings (principally plastic), or furniture, to which they impart a lasting sheen, or still as agents for conditioning textiles.

These compositions can also be used as supports for cosmetic compositions or as cosmetic compositions, and especially as hair lotions. These lotions exhibit principally the surprising property of not imparting to the hair a greasy appearance but, rather, delay the appearance of a greasy aspect to the hair, even though they contain wax as a main active ingredient, in other words, a substance classified as a greasy substance.

Furthermore, it was not obvious that it would be possible to obtain wax microemulsions in the presence of a cationic emulsifier. It is known indeed that waxes which are imperatively present in the composition and which are used alone or as a mixture with other waxes, contain nearly always free fatty acids. Therefore one could expect that there would be an incompatibility between cationic surfactants and waxes having an anionic characteristic.

Therefore, the present invention relates to a fluid composition provided in the form of a wax dispersion in a liquid vehicle comprised of a single phase, wherein the dispersed phase is a stable microdispersion comprised of particles having a size less than 0.5 µm, the said particles being essentially comprised of a mixture of at least one wax, at least one emulsifying agent and optionally at least one oil and/or at least one liposoluble active ingredient, the said mixture having an end melting point greater than 50° C. and lower than 100° C., the said composition containing, by weight, from 0.1 to 40% of wax and from 0.01 to 25% of said emulsifying agent, the said emulsifying agent being a cationic emulsifier, and the concentration of said oil, when it is present, being lower than or equal to 30% by weight relative to the weight of the wax or the mixture of waxes.

The wax or the mixture of waxes employed, in accordance with the present invention, must be able to provide, in combination with the cationic emulsifying agent, according to the process described above, stable microdispersions having particle sizes that are less than 0.5 micrometer. The waxes or mixtures of usable waxes can be selected by simple routine experiments.

In particular embodiments of the present invention the compositions can also exhibit the following characteristics, singly or in combination:

the wax is a wax chosen from Carnauba wax, Candelilla wax, Alfa wax and their mixtures;

the wax contains, in addition to Carnauba wax or Candelilla wax or their mixtures, another wax or a mixture of other waxes, for instance a wax, such as, paraffin wax, ozokerite, hydrogenated jojoba wax, bees wax optionally esterified, rice wax or ceramides including unsaturated ceramids; the weight proportion of Carnauba and/or Candelilla wax, in such mixtures, being preferably greater than or equal to 50%;

the proportion of wax in the composition can vary from 0.1 to 20 weight percent, and especially from 1 to 20%;

the said cationic emulsifying agent is characterized by an HLB value ranging from 11 to 16; the preferred cationic surfactants are quaternary ammonium derivatives; examples of such cationic surfactants are provided in the experimental section hereafter;

the emulsifying agent is present at a concentration of 0.1 to 10 weight percent;

the said liquid vehicle contains between 70 and 100 weight percent water relative to the weight of the liquid phase;

the aqueous vehicle is comprised of water;

the wax/emulsifier weight ratio can vary in the range of 1 to 20 and principally 2 to 10;

the liposoluble active ingredients are, for instance, liposoluble coloring agents, or liposoluble solar filters (substances able to confer protection to a substrate such a skin and/or hair against the harmful effects of ultraviolet radiation); the concentration of the liposoluble active ingredients, when they are present, can range up to 30% (usually up to 10%) by weight relative to the wax or to the mixture of waxes;

at least one amphiphile compound (non wax emulsifying) such as cholesterol, fatty alcohols containing at least 17 carbon atoms, etc., can be combined with the wax; the concentration of the amphiphile compounds can reach up to 30% (especially up to 10%) by weight relative to the wax;

the composition is free of oil, or indeed the concentration of oil, when it is present, is less than or equal to 10 weight percent relative to the weight of the wax or the mixture of waxes; representative useful oils, include those which are mentioned in the experimental section below; and the total weight amount of wax and non-emulsifying amphiphile compounds optionally present, in the particles (aside from emulsifying agents), is usually greater than 90%, and more often greater than 95%, the remainder being made up of oils and optionally present liposoluble ingredients.

Preferably, the compositions of the present invention do not contain non-ionic and/or anionic surfactants.

The vegetable waxes of Carnauba (extracts of Copernica Cerifera), Candelilla (extracts form Euphorbies Cerifera and Pedilanius Pavonia), and Alfa (extracts from the Stipa Tenacissimo) are commercial products.

The ceramids are the main lipids that comprise intercornecocytary spaces of the stratum corneum. They have been described, in particular, by Downing in Science 1982 p. 1561–2, Vol. 18. Ceramids are used especially in cosmetic compositions as anti-aging agents and as hydrating agents; see, for instance, the Japanese patent application 87.176907. In capillary compositions, they act as hair protection agents; see, for instance, the European patent application 02/78505.

These ceramids are difficult to disperse in cosmetic compositions. As a result of the present invention, it is possible to disperse them at high concentration levels.

The optionally present liposoluble coloring agents include, for instance:

1-nitro-3-amino-4-isopropyl aniline, 1-nitro-2-methyl-3-methylamino-4-methyl aniline, 3-nitro-4-butylamino phenol, 4-hydroxy-3-methyl phenylazo benzene, the product having the formula:

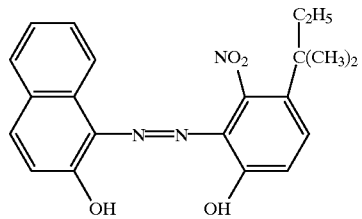

Representative liposoluble solar filters optionally present in the composition of the present invention include in particular the following available products:

3-benzylidene-d,1-camphor, 3-(4'-methyl benzylidene)-d, 1 camphor, amyl 4-(dimethylamine)-benzoate, amyl and isoamyl p-methoxycinnamate and methyl salicylate.

One of the advantages of the composition of the present invention permits the utilization of these liposoluble ingredients in an aqueous medium.

The compositions of the present invention can also constitute supports for compositions, to which other ingredients can be added.

The compositions obtained according to the present invention can contain, especially, one or more conventional secondary ingredients such as thickening agents, pH modifying agents, perfumes, preservatives, or antistatic agents.

The thickening agents must be compatible with the employed cationic surfactants. They are utilized at a concentration such that the viscosity of the composition is at least equal to about 25 poises (or 2.5 Pa.s) at 25° C. (Contraves viscosimeter, measurement body No. 3, rotation time 10 minutes, 200 rpm).

The usable perfumes are typical perfumes, soluble in the wax or dispersible or soluble in water, in particular those that are dispersible or soluble in water. They are generally used at a concentration which does not exceed 5 weight percent.

Optionally present preservatives include, for instance, dimethyloldimethylhydantoin and urea imidazolidinyl derivatives. They are employed in conventionally efficacious amounts.

The pH of the compositions according to the present invention can vary, for instance, from 1 to 13 and preferably from 3 to 11. The pH can optionally be adjusted with a conventional pH regulating agent.

The compositions according to the present invention are obtained by the formation under heat of a microemulsion. More accurately, these compositions are obtained by a process that is mainly characterized by the fact that the mixture of wax and emulsifier is heated to which optionally is added an oil and/or liposoluble substances, at a temperature which is greater than the melting temperature of the mixture and not greater than 100° C., optionally in the presence of a portion of the water, up to complete melting. Water or the remainder of the water, brought to a temperature that is at least equal to the temperature at which the mixture of wax and emulsifier is heated, is gradually added by stirring, until there is formed a wax microemulsion in a continuous aqueous phase. On cooling the microemulsion to ambient temperature a wax microdispersion is formed.

The secondary ingredients optionally present in the composition are added as the case may be either with the starting products, or in the end composition. The liposoluble ingredients are usually added to the wax, before the production of the microdispersion.

The non-volatile hydrosoluble ingredients can optionally be added in the water used for the production of the microdispersion.

The self-lustering compositions for leather items, furniture or ground coatings or coverings, obtained according with the present invention, are applied in accordance with conventional methods, using an absorbing applicator, for instance, one made of felt or expanded plastic foam. The composition can also be applied by pulverization and spread by rubbing the treated surface with a soft fabric.

The textile conditioning compositions, obtained according to the present invention, are applied by mixing with a rinsing liquid.

The cosmetic compositions according to the present invention can principally be used as a styling lotion and also as a lotion intended to improve the aspect of hair of persons who have greasy hair.

They can be applied to dry and clean hair, and also before or after shampooing. They can be rinsed or not rinsed.

When they are applied before or after a shampooing, the application being followed or not by a water rinse, they discipline the hair and impart hold and volume to the hairstyle. Furthermore, they delay a re-oiling phenomenon of the hair observed in subjects with oily hair.

In order to prevent this re-oiling phenomenon, the composition of the present invention can be applied to hair which has been dried after having been washed and, in particular, on that portion of hair close to the roots. In this case, the composition is not rinsed. In spite of an absence of rinsing, it is noted that the composition does not impart to the hair a sticky feeling, and it does not cause a gluing effect of the hair.

Despite the presence of a wax in the composition, no oily appearance is imparted to the hair, even in the absence of rinsing. Furthermore, despite the presence of a high proportion of water in the composition, the drying of the hair does not raise any problems and is effected quickly.

When the compositions contain a liposoluble coloring agent, they can be used as compositions to dye the hair.

It is appropriate to note that the composition supports according to the present invention, which can be diluted in all proportions in water, can be provided in the form of concentrated support compositions which contain high proportions of wax, for instance, from 1 to 40 weight percent.

These concentrated support composition can be diluted at the time of use, in order to obtain a wax concentration ranging, for instance, from 0.1 to 10%.

The secondary ingredients can also be added, after dilution, in the case of concentrated compositions.

The support compositions, obtained according to the present invention, are then, on the one hand, concentrated microdispersions as defined above, which are diluted at the time of use, and on the other hand, nonconcentrated microdispersions (which contain at least water, wax and the surfactant) to which are added at the time of use, the secondary ingredients.

The present invention also relates to a cosmetic treatment process for hair which is designed to improve the hold and the volume of the hairstyle and/or to suppress or delay the appearance of an oily aspect of the hair, characterized by the fact that there is applied at least to a part of the hair near to the roots, a composition such as defined previously, in an amount sufficient to impregnate the hair or the portion of hair to be treated.

This cosmetic treatment process for hair is implemented as shown below.

The following non-limiting examples illustrate the present invention.

EXAMPLES 1 TO 20

Examples of preparing wax microdispersions.

The following procedures are carried out:

The wax and the cationic emulsifying agent are admixed and the mixture is heated to about 90° C. by slowly stirring in order to obtain good homogenization. Water, that has previously been heated to 90° C., is then incorporated by stirring and a microemulsion is thus obtained. The temperature of the wax microemulsion is returned to ambient temperature at which point a microdispersion is formed.

The results obtained with Carnauba wax (10 weight percent, relative to the total weight of the composition) and various cationic emulsifiers are set forth in Table 1.

The granulometric measurements which pertain to the suspended particles (average hydrodynamic diameter) have been carried out by quasi-elastic diffusion of light using a Coulter N4 granulometer laser at 25° C.

TABLE 1

| Examples | Emulsifier | Weight Concentration 5 (%) | Average Diameter of the Particles (nm) |
|---|---|---|---|
| 1 | cetyltrimethyl | 3.33 | 68 |
| 2 | ammonium broiuide | 3.79 | 60 |
| 3 | (CTA) | 2.84 | 149 |
| 4 |  | 3.00 | 74 |
| 5 | CTA chloride | 3.33 | 106 |
| 6 | CTA oxalate | 3.42 | 79 |
| 7 | CTA gallate | 4.72 | 50 |
| 8 | CTA salicylate | 1.75 | 162 |
| 9 | CTA salicylate | 2.63 | 41 |
| 10 | CTA salicylate | 4.38 | 15 |
| 11 | cetylpyridinium bromide (CP) | 4.18 | 43 |
| 12 | CP chloride | 3.72 | 45 |
| 13 | cetyl dimethyl benzyl ammonium chloride (CDBA) | 4.31 | 25 |
| 14 | cetyl-azabicyclo octazonium salicylate | 4.94 | 30 |
| 15 | Arquad 16-50* | 3.33 | 286 |
| 16 | Arquad 18-50* | 3.62 | 303 |
| 17 | Arguad T-50* | 3.62 | 243 |
| 18 | Arquad 2C-75* | 4.35 | 255 |
| 19 | Ethoquad C/12* | 2.50 | 350 |
| 20 | Ethoquad O/12* | 2.50 | 106 |

*Commercial name of quaternary ammonium derivative having a fatty chain and marketed by Armak Chemicals.

EXAMPLES 21 TO 27

In an analogous fashion, microdispersions at 15% Carnauba wax are prepared. The results are set forth in Table II.

TABLE II

| Examples | Emulsifier | Weight Concentration (%) | Average Diameter of the Particles (nm) |
|---|---|---|---|
| 21 | CTA bromide | 2.27 | 179 |
| 22 | CTA bromide | 3.41 | 80 |
| 23 | CTA bromide | 5.00 | 55 |
| 24 | CTA bromide | 5.68 | 51 |
| 25 | cetyl/stearyl- | 3.51 | 83 |
| 26 | dimethyl ethanol ammonium chloride | 5.00 | 71 |
| 27 | myristyltrimethyl ammonium bromide | 3.41 | 147 |

EXAMPLES 28 TO 40

In an analogous fashion, microdispersions at 10% of the wax mixtures are prepared. The cationic surfactant is CTA bromide in each case (3.79% weight percent). The results are set forth in Table III.

TABLE III

| Examples | Waxes, weight percent | | Average Diameter of the particles (nm) |
|---|---|---|---|
| | Carnauba + Paraffin | | |
| 28 | 9 | 1 | 94 |
| 29 | 8 | 2 | 124 |
| 30 | 7 | 3 | 160 |
| | Carnauba + Ozokerite* | | |
| 31 | 9 | 1 | 94 |
| 32 | 7 | 3 | 195 |
| | Carnauba + Candelilla | | |
| 33 | 9 | 1 | 67 |
| 34 | 7 | 3 | 136 |
| | Carnauba + hydrogenated Jojoba wax | | |
| 35 | 9 | 1 | 104 |
| | Carnauba + rice wax | | |
| 36 | 9 | 1 | 97 |
| 37 | 7 | 3 | 173 |
| 38 | 5 | 5 | 197 |
| | Carnauba + Cera Bellina** | | |
| 39 | 9 | 1 | 106 |
| 40 | 7 | 3 | 138 |

*marketed by Quest International
**Esterified bees wax (Quest International)

EXAMPLES 41 TO 43

Wax microdispersions having the following weight composition are prepared:

| Carnauba | 10% |
|---|---|
| Lipophile additive | x% |
| CTA bromide | 3.79% |
| Water, sufficient amount for | 100% |

TABLE IV

| Examples | Lipophile Additive | | Average Diameter (nm) |
|---|---|---|---|
| 41 | Colorant* | 1% | 29 |
| 42 | Parsol MCX | 3% | 350 |
| 43 | Parsol MCX | 2.4% | 256 |
| | Uvinul M40 | 0.6% | |

*2-isopropyl-6-nitro aniline

Parsol MCX is the commercial tradename for octyl methoxy cinnamate, marketed by Givaudan, and utilized as an ultraviolet radiation filtering agent ("solar filter").

Uvinul M40 is the commercial tradename for 3-benzophenone, marketed by BASF and utilized as a solar filter.

The procedure for the preparation is as follows: the wax, the cationic emulsifying agent and the liposoluble active products (coloring agents or solar filter) are admixed. The procedures of Example 1 are then carried out.

EXAMPLES 44 TO 46

In an analogous fashion to that described in Examples 41 to 43, wax microdispersions having the following weight composition were prepared:

| Carnauba wax | x% |
|---|---|
| Oil | y% |
| CTA bromide | 3.79% |
| Water | 86.21% | with x+y=10%

The results are set forth in the following Table V:

TABLE V

| Examples | Wax x | Oil y | Diameter of the Particles (nm) |
|---|---|---|---|
| | Carnauba | paraffin oil | |
| 44a | 9 | 1 | 43 |
| 44b | 7 | 3 | 106 |
| | Carnauba | DV | |
| 45a | 9 | 1 | 29 |
| 45b | 7 | 3 | 39 |
| | Carnauba | Sunflower oil | |
| 46a | 9 | 1 | 85 |
| 46b | 7 | 3 | 174 |

DV: 3-(2-ethyl hexyloxy)-1-hexadecanoyl-2-propanol described in French patent 2222351.

EXAMPLES 47 TO 49

In an analogous fashion, wax microdispersions having the following weight composition were prepared.

| Carnauba wax | x% |
|---|---|
| Ceramid and/or cholesterol | y% |
| CTA bromide | 3.79% |
| Water | 86.21% |

The results are set forth in the following table VI:

TABLE VI

| Examples | Wax + Lipophile Compound in weight percent | | | Average Diameter of Particles (nm) |
|---|---|---|---|---|
| | Carnauba + DVA* | | | |
| 47 | 8 | 2 | | 123 |
| | Carnauba + cholesterol | | | |
| 48a | 9 | 1 | | 91 |
| 48b | 8 | 2 | | 196 |
| | Carnauba + DVA + cholesterol | | | |
| 49 | 8 | 1 | 1 | 129 |

*DVA: Ceramid having the formula $C_{15}H_{31}CHOHCH(CH_2OH)NHCOC_{15}H_{31}$ (erythro:threo mixture)

Examples of Preparation of Cosmetic Compositions
EXAMPLE 1c: Capillary Lotion
This lotion was prepared by mixing in order the following constituents:

| | |
|---|---|
| 10% wax microdispersion obtained in Example 1 | 97.3 g |
| Methyl parahydroxybenzoate | 0.1 g |
| Derivative of imidazolidinylurea sold under the tradename "SUTTON CAPS" | 0.2 g |
| NaOH, sufficient amount for pH = 6.8 | |
| Water, sufficient amount for | 100 g |

This lotion is applied after washing and drying the hair at a rate of about 2 g per head.
The hair has volume, and is well disciplined.
EXAMPLE 2c: Capillary Lotion
Operating in the manner as described in Example 1c, the following constituents were employed:

| | |
|---|---|
| 15% wax microdispersion obtained in Example 15 | 70 g |
| Methyl parahydroxybenzoate | 0.15 g |
| "GERMALL 115" | 0.2 g |
| NaOH, sufficient for pH = 7 | |
| Water, sufficient amount for | 100 g |

This lotion is applied to clean and dry hair and imparts thereto fullness and sheen.
EXAMPLES 3c AND 4c: Hair Styling Gel
These gels have the following weight composition:

| | Example 3c | Example 4c |
|---|---|---|
| Microdispersion of Example 22 | 12 g | 12 g |
| Methyl hydroxypropyl cellulose, marketed as "METHOCEL 60 HG" by Dow Corning | 2.20 g | |
| Hydroxyethyl cellulose marketed under the name of "NATROSOL 250 HRR" by Aqualon | | 1.20 g |
| Methyl p.hydroxybenzoate | 0.15 g | 0.15 g |
| DOWICIL 200 - Dow Corning | 0.3 g | 0.3 g |
| Water, sufficient amount for | 100 g | 100 g |

These styling gels are applied to clean and dry hair along the entire length of hair including the roots at a rate of 2 to 5 g per head.
The gels are easily spread on the hair which has a silky touch and fullness and is puffy and disciplined.
EXAMPLE 5c: Capillary Lotion
This lotion is prepared by mixing in order the following constituents:

| | |
|---|---|
| Wax microdispersion obtained in Example 41 | 95 g |
| Methyl parahydroxybenzoate | 0.15 g |
| "GERMALL 115" | 0.2 g |
| NaOH, sufficient amount for pH = 6.8 | |
| Water, sufficient amount for | 100 g |

This solution (about 2 g/head) is applied, strand by strand, to dry unwashed hair and is permitted to remain in contact therewith for 5 minutes before effecting a shampoo. The hair exhibits volume and discipline and is colored yellow.
EXAMPLE 6c: Capillary Lotion
The procedures of Example 1c are repeated using the following constituents:

| | |
|---|---|
| Wax microdispersion obtained in Example 43 | 97 g |
| Methyl parahydroxybenzoate | 0.1 g |
| "GERMALL 115" | 0.2 g |
| NaOH, sufficient for pH = 6.8 | |
| Water, sufficient amount for | 100 g |

This composition is applied to clean and dry hair, on the roots and throughout the length of the hair at a rate of 2 g per head.
The hair is soft, it exhibits discipline and is puffy. The application of the composition also imparts to the hair a protective effect with regard to UV radiation.
EXAMPLE 7c
This lotion is prepare by mixing in order the following constituents:

| | |
|---|---|
| Wax microdispersion obtained in Example 46a | 95 g |
| Methyl parahydroxybenzoate | 0.15 g |
| "GERMALL 115" | 0.2 g |
| NaOH, sufficient for pH = 6.9 | |

The application of this composition on dry and clean hair gives the hairdo puff and sheen.
EXAMPLE 8c
The procedures of Example 1c are repeated using the following constituents:

| | |
|---|---|
| Wax microdispersion obtained in Example 49 | 97 g |
| Methyl parahydroxybenzoate | 0.1 g |
| "GERMALL 115" | 0.2 g |
| NaOH, sufficient for pH = 7 | |
| Water, sufficient amount for | 100 g |

This composition is applied after shampoo. The hair exhibits good hold, is disciplined and is full-bodied.

We claim:
1. In a process for preparing a microdispersion of solid wax particles in an aqueous vehicle by melting wax in the presence of a surfactant and optionally a portion of water, and progressively adding hot water with stirring until an oil-in-water type emulsion is formed, and cooling to obtain a stable microdispersion of solid colloidal wax particles, the improvement comprising using a surfactant consisting of a quaternary ammonium cationic surfactant having an HLB value ranging from 11 to 16, as said surfactant.

2. The process of claim 1 wherein said melting is performed in the presence of at least one of:
   (i) at least one liposoluble active ingredient in an amount up to 30% by weight relative to the weight of said at least one wax,
   (ii) at least one oil in an amount up to 30% relative to the weight of said at least one wax, and
   (iii) at least one amphiphilic non wax-emulsifying compound in an amount up to 30% by weight relative to the weight of said at least one wax.

3. A process for preparing a composition comprising a stable microdispersion of solid particles in a single phase aqueous vehicle, wherein said solid particles consist essentially of a mixture of:
   at least one wax in an amount ranging from 0.1 to 40% by weight relative to the weight of the composition,
   a surfactant consisting of at least one quaternary ammonium cationic surfactant having an HLB value ranging from 11 to 16, in an amount ranging from 0.01 to 25% by weight relative to the composition,
   optionally at least one liposoluble active ingredient in an amount up to 30% by weight relative to the weight of said at least one wax,
   optionally at least one oil in an amount up to 30% relative to the weight of said at least one wax, and
   optionally at least one amphiphilic non wax-emulsifying compound in an amount up to 30% by weight relative to the weight of said at least one wax,
   said mixture having an end melting point greater than 50° C. and lower than 100° C.,
   and wherein said composition is free of anionic and non ionic surfactants,
   said process consisting essentially of:
   mixing said at least one wax, said cationic surfactant and optionally said oil, said amphiphilic compound and/or said liposoluble active ingredient,
   heating the obtained mixture, optionally in the presence of a portion of water, at a heating temperature lower than 100° C., up to complete melting,
   progressively adding, with stirring, water, or the remainder of water, heated to said heating temperature, until there is formed a wax microemulsion in a continuous aqueous phase whereby cooling said microemulsion to ambient temperature results in a microdispersion of solid particles having a size less than 0.5 $\mu$m.

4. A cosmetic treatment process to improve the shape and body of a hair style or to suppress or delay the appearance of an oily aspect of hair, or both, comprising applying to the hair, in an amount sufficient to impregnate the hair,
   a stable wax microdispersion consisting of a single liquid phase and a solid dispersed phase, said microdispersion being free of anionic and nonionic surfactants, said solid dispersed phase comprising solid particles having a size of less than 0.5 $\mu$m, said solid phase consisting essentially of at least one wax in an amount in the range of 0.1 to 40% by weight of said microdispersion, a surfactant consisting of at least one quaternary ammonium derivative having an HLB value in the range of 11 to 16, said surfactant being present in an amount in the range of 0.01 to 25% by weight of said microdispersion and, optionally, at least one oil or liposoluble active ingredient, said oil being present in an amount in the range of 0 to 30 weight percent relative to the weight of wax.

5. The process according to claim 4 wherein said stable wax microdispersion is free of oil.

6. The process according to claim 4 wherein said wax is selected from the group consisting of Carnauba wax, Alfa wax and mixtures thereof, and optionally, at least one wax selected from the group consisting of paraffin wax, ozokerite, hydrogenated jojoba wax, rice wax, esterified beeswax and mixtures thereof.

7. The process according to claim 4 wherein said liquid phase contains 70 to 100 weight percent water.

8. A microdispersion prepared according to the process of claim 1.

9. A composition prepared according to the process of claim 3.

10. A stable wax microdispersion consisting of a single liquid phase and a solid dispersed phase, said microdispersion being free of anionic and nonionic surfactants, said solid dispersed phase comprising solid particles having a size of less than 0.5 $\mu$m, said solid dispersed phase consisting essentially of at least one wax in an amount in the range of 0.1 to 40% by weight of said microdispersion, a surfactant consisting of at least one quaternary ammonium cationic surfactant having an HLB value ranging from 11 to 16 wherein said cationic surfactant is present in an amount in the range of 0.01 to 25% by weight of said microdispersion and, optionally, at least one oil or liposoluble active ingredient, said oil being present in an amount in the range of 0 to 30 weight percent relative to the weight of wax.

11. A cosmetic treatment process to suppress or delay the appearance of an oily aspect of hair comprising applying to the hair of a person, in an amount sufficient to impregnate the hair,
   a stable wax microdispersion consisting of a single liquid phase and a solid dispersed phase, said microdispersion being free of anionic and nonionic surfactants, said solid dispersed phase comprising solid particles having a size of less than 0.5 $\mu$m, said solid phase consisting essentially of at least one wax in an amount in the range of 0.1 to 40% by weight of said microdispersion, a surfactant consisting of at least one quaternary ammonium surfactant having an HLB value ranging from 11–16 wherein said cationic surfactant is present in an amount in the range of 0.01 to 25% by weight of said microdispersion and, optionally, at least one oil or liposoluble active ingredient, said oil being present in an amount in the range of 0 to 30 weight percent relative to the weight of wax.

* * * * *